United States Patent
Kennedy

(10) Patent No.: US 6,989,135 B2
(45) Date of Patent: Jan. 24, 2006

(54) HYDROCARBON CONVERSION SYSTEM WITH ENHANCED COMBUSTOR AND METHOD

(75) Inventor: Paul E. Kennedy, Tulsa, OK (US)

(73) Assignee: Syntroleum Corporation, Tulsa, OK (US)

(*) Notice: Subject to any disclaimer, the term of this patent is extended or adjusted under 35 U.S.C. 154(b) by 828 days.

(21) Appl. No.: 09/877,286

(22) Filed: Jun. 8, 2001

(65) Prior Publication Data

US 2001/0044476 A1 Nov. 22, 2001

Related U.S. Application Data

(62) Division of application No. 09/596,285, filed on Jun. 15, 2000, now Pat. No. 6,265,453.

(60) Provisional application No. 60/141,989, filed on Jul. 1, 1999.

(51) Int. Cl.
*B01J 8/04* (2006.01)

(52) U.S. Cl. .................. 422/198; 422/190; 422/211; 518/703; 518/702; 518/700; 60/39.12; 341/144

(58) Field of Classification Search ............... 518/703; 422/211, 190; 60/39.05
See application file for complete search history.

(56) References Cited

U.S. PATENT DOCUMENTS

| | | | |
|---|---|---|---|
| 4,833,170 A | 5/1989 | Agee | 518/703 |
| 4,973,453 A | 11/1990 | Agee | 422/190 |
| 5,490,377 A | 2/1996 | Janes | 60/39.12 |
| 5,666,800 A | 9/1997 | Sorensen et al. | 60/39.02 |
| 5,694,761 A | 12/1997 | Griffin, Jr. | 60/39.05 |
| 5,733,941 A | 3/1998 | Waycuilis | 518/703 |
| 5,861,441 A | 1/1999 | Waycuilis | 518/703 |
| 5,973,631 A | 10/1999 | McMullen et al. | 341/144 |
| 5,980,840 A | 11/1999 | Kleefisch et al. | 422/211 |

FOREIGN PATENT DOCUMENTS

EP 0110486 A1 * 6/1984
WO WO 98.01514 1/1998

OTHER PUBLICATIONS

"PFBC clean-coal technology. A new generation of combined-cycle plants to meet the growing world need for clean cost effective power." ABB Carbon Marketing Department, S-612 82 Finspong, Approximately Feb. 1998.
Simon et al, Energy Convers. Manage. (1997), 38 (15-17), 1671-1679, 1997.

* cited by examiner

Primary Examiner—Alexa Doroshenk
Assistant Examiner—Vinit H. Patel
(74) Attorney, Agent, or Firm—Baker Botts L.L.P.

(57) ABSTRACT

A Fischer-Tropsch-based hydrocarbon conversion process involves compressing air in a compressor section of a gas turbine, delivering a portion of the compressed air to a combustor of the gas turbine, delivering a portion of the compressed air to a Fischer-Tropsch hydrocarbon conversion unit, extracting thermal energy from the combustor and delivering it to the Fischer-Tropsch hydrocarbon conversion unit, converting light hydrocarbons into heavier hydrocarbons in the Fischer-Tropsch hydrocarbon conversion unit, and delivering combustion gases from the combustor to an expansion section of the gas turbine. A heat recovery steam generator (HRSG) may also be used to harness waste heat from the expansion section. A conversion system for converting light hydrocarbons into heavier hydrocarbons includes a turbine from which heat energy is removed and used to assist in converting hydrocarbons and whereby greater throughput of the turbine is possible. Waste heat from the expander of the turbine may be recovered with a HRSG.

3 Claims, 4 Drawing Sheets

HYDROCARBON CONVERSION SYSTEM WITH ENHANCED COMBUSTOR AND METHOD

RELATED APPLICATIONS

This application claims the benefit of U.S. provisional application U.S. Ser. No. 60/141,989 filed Jul. 1, 1999.

This application is a divisional of U.S. application Ser. No. 09/596,285, filed Jun. 15, 2000, now U.S. Pat. No. 6,265,453 by Paul E. Kennedy and entitled "Hydrocarbon Conversion System with Enhanced Combustor and Method".

TECHNICAL FIELD OF THE INVENTION

The present invention relates to hydrocarbon conversion systems, and more particularly to a Fischer-Tropsch-based system with an enhanced turbine combustor.

BACKGROUND OF THE INVENTION

Gas turbines are used in many applications including gas-turbine-driven powerplants. The gas turbine exhaust has been used to improve the overall powerplant performance by taking the high temperature turbine exhaust and recovering the heat. It is normally recovered by conventional steam generating techniques, e.g., boiler, and routed to a steam turbine. The condensed steam may be recycled to the boiler. This arrangement is typically called a combined cycle powerplant. "Cogeneration" refers generally to the simultaneous on-site generation of electric energy and process steam or heat from the same plant. As described further below, as an aspect of the present invention, a cogeneration system is novelly incorporated into a Fischer-Tropsch-based system.

The synthetic production of hydrocarbons by the catalytic reaction of carbon monoxide and hydrogen is well known and is generally referred to as the Fischer-Tropsch reaction. The Fischer-Tropsch process was developed in early part of the $20^{th}$ century in Germany. It was practiced commercially in Germany during World War II and has been practiced in South Africa for some time. An ongoing quest has existed, however, to improve the economics of the process.

The Fischer-Tropsch-based conversion process may first involving converting light hydrocarbons (such as methane) into synthesis gas (primarily CO and $H_2$) and then converting the synthesis gas to heavier hydrocarbons through the Fischer-Tropsch reaction. The hydrocarbon products derived from the Fischer-Tropsch reaction range from some methane to high molecular weight paraffinic waxes containing more than 50 carbon atoms, but primarily includes C5+.

Numerous Fischer-Tropsch catalysts, such as iron and cobalt catalysts, have been used in carrying out the reaction, and both saturated and unsaturated hydrocarbons can be produced. Numerous types of systems and reactors have been used for carrying out the Fischer-Tropsch reaction. See, for example, U.S. Pat. Nos. 4,883,170 and 4,973,453, which are incorporated herein by reference for all purposes.

It has been a quest for some time to improve the economics of hydrocarbon conversion systems, particularly those utilizing the Fischer-Tropsch reaction. Improved economics will allow wide-scale adoption of the process in numerous sites and for numerous applications. These efforts are reflected in U.S. Pat. Nos. 5,733,941 and 5,861,441, which are incorporated herein by reference for all purposes.

One particular challenge to improved performance is related to the thermal limitations of gas turbines that are included in some embodiments of Fischer-Tropsch systems. The turbine blades can only withstand a certain level of heat. This in turn limits the throughput since the oxygen-containing gas supplied to the turbine expander must be limited to control the temperature.

SUMMARY OF THE INVENTION

Therefore, a need has arisen for an improved hydrocarbon conversion system that addresses shortcoming of previous conversion systems. According to an aspect of the present invention, a method for converting light hydrocarbons into heavier hydrocarbons includes the steps of: compressing air in a compressor section of a gas turbine; delivering a portion of the compressed air to a combustor of the gas turbine; delivering a portion of the compressed air to a Fischer-Tropsch hydrocarbon conversion unit; extracting thermal energy from the combustor and delivering it to the Fischer-Tropsch hydrocarbon conversion unit; converting light hydrocarbons into heavier hydrocarbons in the Fischer-Tropsch hydrocarbon conversion unit; and delivering combustion gases from the combustor to an expansion section of the gas turbine. According to another aspect of the present invention a heat recovery steam generator (HRSG) may be used to harness waste heat from the expansion section of the turbine.

According to another aspect of the present invention, a Fischer-Tropsch-based system for converting light hydrocarbons into heavier hydrocarbons includes a gas turbine having a compressor section, combustor, and expander section, and having a compressed air conduit; a Fischer-Tropsch hydrocarbon conversion subsystem for converting light hydrocarbons into heavier hydrocarbons; a heat removal subsystem associated with the combustor for thermally coupling the hydrocarbon conversion subsystem to the combustor to deliver thermal energy from the combustor to the hydrocarbon conversion subsystem; and a process air conduit fluidly coupled between the compressed air conduit and the Fischer-Tropsch hydrocarbon conversion subsystem, the process air conduit for delivering a portion of the compressed air developed by the compressor section to the Fischer-Tropsch hydrocarbon conversion subsystem. According to another aspect of the present invention, a HRSG is included to recover energy from the expansion section exhaust.

A technical advantage of the present invention is that it allows for more thorough combustion (and thus more efficiency) by the combustor, e.g., the $O_2$ content of the turbine exhaust may go from 10–14% to as low as 2%. Other technical advantages exist.

BRIEF DESCRIPTION OF THE DRAWINGS

For a more complete understanding of the present invention and advantages thereof, reference is now made to the following description taken in conjunction with the accompanying drawings in which like reference numbers indicate like features, and wherein.

DETAILED DESCRIPTION OF THE INVENTION

The preferred embodiment of the present invention and its advantages are best understood by referring to FIGS. 1–4 of the drawings, like numerals being used for like and corresponding parts of the various drawings.

The systems and techniques described herein may be used with numerous hydrocarbon conversion processes and systems that include a gas turbine, but preferably are used with a Fischer-Tropsch-based hydrocarbon conversion system. In many applications involving a gas turbine, attention must be given to maintaining the temperature of the gases exiting the turbine combustor under some predetermined level. This requirement stems primarily from inlet temperature limitations for the expander. The turbine has thermal failure limits based on the components in it, and further, limits may exist based on acceptable levels of nitrogen oxides, $NO_x$, in the exhaust. The combustor outlet temperature may be reduced by increasing the air (or adding other diluents such as steam or any noncombustable gas) provided to the combustor or by limiting the fuel provided to the combustor. As an important aspect of the invention, it has been found to be advantageous now to use techniques and devices to remove heat from the combustor. As another important aspect of the invention, a heat recovery steam generator subsystem may be used to recovery heat from the turbine exhaust to improve performance of plants for power generation and a hydrocarbon conversion process.

Figure 1:
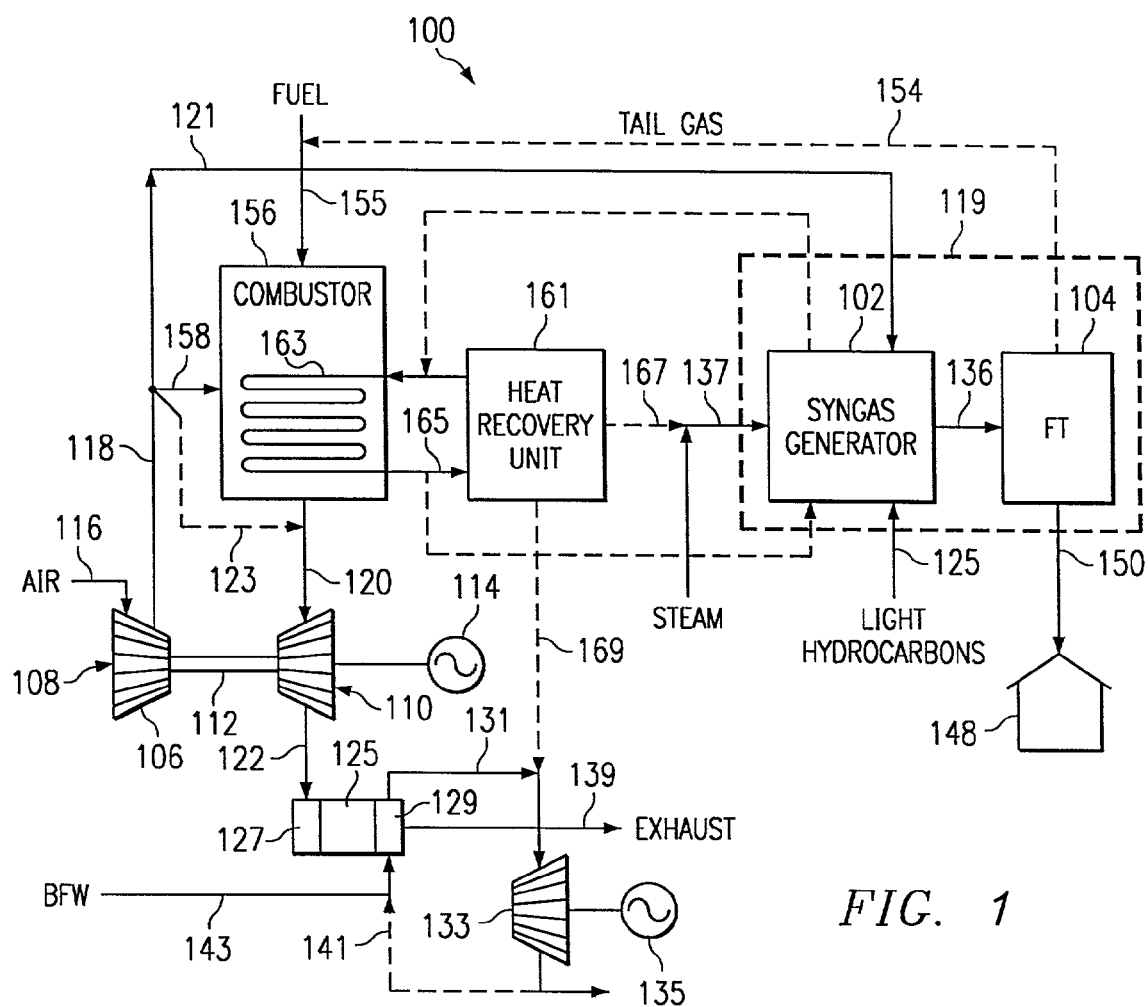
FIG. 1 is a schematic flow diagram of an embodiment of the present invention including a hydrocarbon conversion subsystem.

Referring now to FIG. 1, there is shown a Fischer-Tropsch-based hydrocarbon conversion system 100 that includes a heat removal unit 161 for removing heat from a combustor 156 of a gas turbine 106 and uses the heat in a hydrocarbon conversion subsystem 119. Heat removed from the turbine 106 exhaust may also be recovered and used through a heat recovery unit 125 and associated steam turbine 133.

The hydrocarbon conversion subsystem or unit 119 includes a synthesis gas generator unit (or synthesis gas unit) 102 and a synthesis gas conversion unit (or synthesis unit) 104. System 100 uses the gas turbine 106 to provide power for the system 100 at a minimum, but preferably provides additional power as a net exporter of power.

Gas turbine 106 has compressor section 108 and an expansion turbine section 110. Expansion section 110 drives compressor section 108 by means of a linkage 112 (e.g., a shaft) and any excess power is used to generate electricity or drive other equipment (or for export) as shown by load output 114. Compressor 108 has inlet conduit 116 where it receives air and an outlet conduit 118. Compressed air in conduit 118 is delivered to combustor 156 through conduit 158. It is also preferably delivered through conduit 121 to the hydrocarbon conversion subsystem 119, which includes synthesis gas generator 102 and Fischer-Tropsch synthesis unit 104. The compressed air in conduit 118 may further be delivered through conduit 123 to conduit 120 to provide further cooling of gasses before they enter turbine expander 110 or may be delivered directly to the turbine expander to cool its turbine blades. The exhaust from turbine 110 is delivered into conduit 122, which in turn delivers the exhaust to a heat recovery steam generator (HRSG) unit 125. HRSG 125 may include a burner portion 127 and a steam generation portion 129. Boiling feedwater is supplied to steam generator 129 through conduit 143. Steam produced in the HRSG 125 is delivered through conduit 131 to a steam turbine 133. The steam generated is preferably between 250–1300 deg. F. and at 50 to 4000 psig, and more preferably between 50 to 400 psig. Steam turbine 133 drives the power offtake 135, which may be used to power other items within system 100, or may be used to export power. The steam exhaust may go through a condenser, and the resultant condensate may be delivered through conduits 141 and 143 to HRSG 125. The gas turbine exhaust exiting HRSG 125 exits through conduit 139.

Focusing on the hydrocarbon conversion unit 119, synthesis gas unit 102 may take a number of configurations, but in the preferred embodiment, includes an autothermal reformer. Synthesis gas unit 102 receives light hydrocarbons, such as natural gas, through conduit 125 and steam through conduit 137. These inputs plus the compressed air of conduit 121 (air is preferred but it may also be enriched air, or any oxygen containing gas) are used in producing synthesis gas in unit 102 that is delivered through conduit 136 to Fischer-Tropsch synthesis unit 104. Numerous other components known in the art are not shown for simplicity here, such as heat exchangers and separators. Synthesis unit 104 is used alone or with further downstream processing to make a plethora of products such as those mentioned further below.

Synthesis unit 104 is analogous to that described in connection with FIGS. 2–3. Synthesis unit 104 includes a Fischer-Tropsch reactor used to make a heavier product ($C_{5+}$), which is delivered through conduit 150 to a storage unit 148 or for further downstream processing. A low-Btu residue or tail gas (preferably $C_5$ and less and <120 Btu/SCF) may be delivered through conduit 154 to combustor 156 for use a fuel therein.

Combustor 156 receives fuel through conduit 155. The fuel provided to conduit 155 may be light hydrocarbons, synthesis gas (e.g., from a gasifier or from another system such as shown in FIG. 4 below), coal, fuel oil, or other acceptable combustor fuel, and preferably is a tail gas from the hydrocarbon conversion unit 119. Combustor 156 preferably burns a fuel with compressed air from conduit 158 to generate exhaust delivered through conduit 120. The gases exiting the combustor are preferably in the range of 1400–2400 deg. F. and a pressure of 100 to 500 psig. As an important aspect of the present invention, a portion of the heat developed in combustor 156 is removed through a heat recovery unit 161. Heat recovery unit 161 may include internal heat exchangers 163 within combustor 156 and necessary conduits 165 to allow a medium to remove heat from within combustor 156. For the embodiment shown, the heat recovery unit circulates a boiling feed water through exchanger 163 that is used to generate steam that is delivered to heat recovery unit 161, which may then be delivered through conduit 167 to the synthesis gas generator 102 to help with the production of synthesis gas. In addition, another portion or the remaining portion of the steam generated may be delivered through conduit 169 to steam turbine 133 for use in production of power therein.

Heat recovery unit 161 may take numerous embodiments and may be an aspect of hydrocarbon conversion unit 119 itself. The removed heat may be used to generate steam, combined directly as a heat exchanger in a steam methane reformer, or otherwise used within hydrocarbon conversion unit 119. Treated byproduct water from unit 119 may be used by heat recovery unit 161.

The addition of the heat removal unit 161 to combustor 156 allows for greater amounts of compressed air to be extracted through conduit 121 without the turbine inlet temperature getting too high. With the embodiment of FIG. 1, for example, it has been found through simulations that as much as about 35% of the air may be extracted to the synthesis gas generator without heat removal, but with the embodiment of FIG. 1 with heat removal, as much as 65% or more of the air may be extracted. This in turn allows for the oxygen content in conduit 122 to be reduced to less than 10 volume percent and preferably less than 2 volume percent. The benefits of a system like system 100 have been suggested by preliminary computer modeling. The modeling is presented in reference to the embodiment of FIG. 2.

Figure 2:
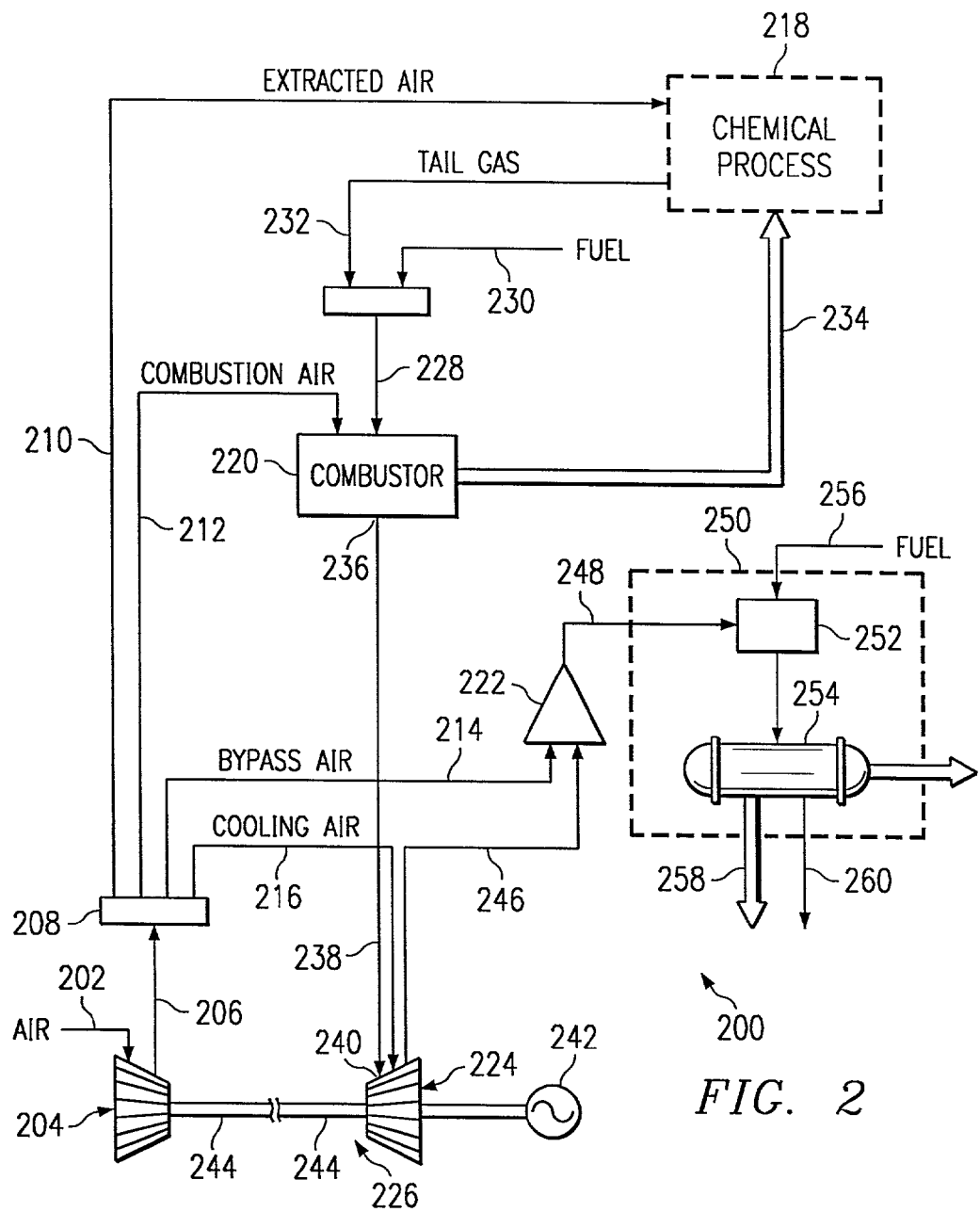
FIG. 2 is a schematic diagram of a third embodiment of the present invention.

Referring now to FIG. 2, a system 200 for converting light hydrocarbons into heavier hydrocarbons is presented. System 200 receives filtered air through air inlet 202. Compressor section 204 of a gas turbine 226 compresses the air. The compressed air is delivered to outlet 206. Outlet 206 delivers the compressed air to distributor manifold 208. The air is distributed by manifold 208 to four air conduits 210, 212, 214, and 216.

If desired, conduit 210 is used to deliver compressed air to a hydrocarbon conversion unit 218, which is preferably a Fischer-Tropsch hydrocarbon conversion unit. Conduit 212 delivers at least a portion of the compressed air to combustor 220 of gas turbine 226. Conduit 214 is a bypass conduit that delivers a portion of the air to connector 222. Conduit 216 provides cooling air to expander section or turbine 224 of gas turbine 205.

Combustor 220 may be formed adjacent to or as an integral part of turbine 224. Compressor 204, combustor 220, and turbine 224 form gas turbine 226. Combustor 220 receives a fuel mixture through conduit 228. Conduit 228 receives a combustor fuel through conduit 230 and may receive a tail gas fuel from chemical process 218 through conduit 232. According to an important aspect of the present invention, a heat removal subsystem is associated with combustor 220 and removes heat; heat removal from combustor 220 is shown by energy flow 234. The energy flow shown by 234 is preferably used by conversion unit 218. It may be used, for example, to create additional synthesis gas to be fed to a Fischer-Tropsch reactor. The exhaust gases from the combustor 220 are delivered through outlet 236 and conduit 238 to turbine inlet 240.

Turbine/expander 224 receives the pressurized hot exhaust products from combustor conduit 236 and expands them to drive a load, such as a generator 242, and to drive compressor 204 through linkage or shaft 244. The turbine exhaust is delivered to turbine outlet 246, which delivers them to connector 222. Turbine 224 receives cooling air for cooling blades and components through conduit 216. The turbine exhaust and any bypass air are then delivered to conduit 248. Conduit 248 delivers the exhaust and gases to a heat recovery steam generator (HRSG) subsystem 250.

HRSG 250 includes a burner 252 and a combustion can/steam generator 254. Burner 252 receives burner fuel through conduit 256. The energy generated in HRSG 250 is removed by energy flow 258; a generator may be used to harness the energy of flow 258. The effluent gas products are shown exiting through conduit 260.

To compare, contrast, and highlight advantages of different aspects of the present invention, four cases were considered in a computer simulation model conducted on a HYSYS simulation package (from Hyprotech Ltd.). In conducting this analysis, the following assumptions were made: (1) The temperature of the turbine inlet 240 was held constant at 1,979 deg. F; (2) Compressor 204 and expander 224 were assumed to have constant efficiencies for all cases of 84.7% and 88% respectively; (3) The turbine inlet pressure 240 was held the same for all cases at 180 psia; (4) Compressor outlet pressure at 206 was assumed to be a function of the mass through expander 224 and to increase slightly as the mass flow from the combustor 220 to the turbine increases (e.g., 188 psia versus 185 psia); (5) The pressure drop through combustor 220 was assumed to increase slightly for cases in which energy 234 is removed from the combustor 220 (e.g., 8 psia vs. 5 psia); (6) Stack exhaust 260 was held constant at 500 deg. F. for cases in which system 200 is considered with HRSG 250 in operation; (7) Stack exhaust 260 is assumed to have a constant 2 vol. % $O_2$ for cases in which the HRSG 250 is considered to be in operation; (8) The pressure drop was assumed to increase slightly for duct burner 252 in the HRSG 250 (0.43 psia vs. 0.36 psia); (9) The air mass was assumed to remain constant for all cases at 2,315,000 LB/hr.; and (10) The fuel gas heating value was assumed to be 907.7 Btu/SCF for all cases.

With these assumptions four cases were considered. Case A was without energy removal 234 and without HRSG 250 in operation. Case B was with energy removal 234 from combustor 220, but without HRSG 250 operational. Case C was the same as Case B, but with HRSG 250 operational. Finally, Case D was the same as Case A but with the HRSG 250 operational. The results of the model are as follows:

|  | Case A | Case B | Case C | Case D |
|---|---|---|---|---|
| Air 202 |  |  |  |  |
| Temp, F. | 59 | 59 | 59 | 59 |
| Pres., psia | 14.57 | 14.57 | 14.57 | 14.57 |
| Comb. Fuel 228 |  |  |  |  |
| Temp., F. | 60.0 | 60.0 | 60.0 | 60.0 |
| Pres., psia | 195.00 | 195.00 | 195.00 | 195.00 |
| Flow, MSCFH | 980.25 | 2820.06 | 2820.06 | 980.25 |
| Comb. Outlet 236 |  |  |  |  |
| Temp., F. | 1979.0 | 1979.0 | 1979.0 | 1979.0 |
| $O_2$ % | 13.77 | 2.00 | 2.00 | 2.00 |
| Pres. Drop, psia | 5.0 | 8.0 | 8.0 | 5.0 |
| Energy 234 (MMBTU/HR) | 0.00 | 1532.00 | 1532.00 | 0.00 |
| Duct Burner 252 |  |  |  |  |
| Fuel Temp., F. | 60.0 | 60.0 | 60.0 | 60.0 |
| Pres., psia | 25.00 | 25.00 | 25.00 | 25.00 |
| Flow, MSCFH | 0.0 | 0.0 | 0.0 | 1839.82 |
| Pres. Drop, psia | 0.00 | 0.00 | 0.00 | 0.07 |
| Energy MMBTU/HR HRSG 250 | 0.00 | 0.00 | 0.00 | 1670.00 |
| Energy 258 | 0.00 | 0.00 | 387.60 | 1971.00 |
| Pres. Drop., psia | 0.00 | 0.00 | 0.36 | 0.36 |
| Exhaust 260 |  |  |  |  |
| Temp., F. | 1007.0 | 1046.0 | 500.0 | 500.0 |
| Pres., psia | 14.70 | 14.70 | 14.70 | 14.70 |
| Flow, lb/hr. | 2358000.0 | 2440000.0 | 2440000.0 | 2440000.0 |
| O2 % | 13.77 | 2.00 | 2.00 | 2.00 |
| Pres. Drop, psia | 0.00 | 0.000 | 0.00 | 0.00 |
| Compr. 206 |  |  |  |  |
| Pres., psia | 185.00 | 188.00 | 188.00 | 185.00 |
| Temp., F. | 696.5 | 702.0 | 702.0 | 696.5 |
| Power, HP | 143500.0 | 144700.0 | 144700.0 | 143500.0 |

-continued

| HRSG 250 operational. The results of the model are as follows: | | | | |
|---|---|---|---|---|
| | Case A | Case B | Case C | Case D |
| Gas Turbine 224 | | | | |
| Outlet Temp., F. | 1007.0 | 1046.0 | 1053.0 | 1021.0 |
| Outlet Pres., psia | 14.70 | 14.70 | 15.06 | 15.13 |
| Power,HP Generator 242 | 262580 | 282180 | 280170 | 259110 |
| Gross Power, KW | 88798 | 102519 | 101020 | 86210 |
| Energy 234 & 258 | 0 | 133217 | 166922 | 171391 |
| Total Fuel, MMBTU/Hr | 889.77 | 2559.77 | 2559.77 | 2559.77 |
| Total KW/Btu/Hr. | 99.798 | 92.092 | 104.674 | 100.634 |

As shown by the above chart, Case C, the embodiment that includes heat removal 234 from the combustor 220 and an operational HRSG 250, produces the best result with respect to total KW/Btu/Hr. for this model.

In a preferred embodiment, the conversion processes used as part of the present invention, e.g., process 218 of FIG. 2, converts synthesis gas into heavier, longer-chain hydrocarbons. This is preferably accomplished using a Fischer-Tropsch process. The Fischer-Tropsch catalyst may be an alumina supported cobalt catalyst, or other FT catalyst such as iron or ruthenium. Other conversion options may be used as well. The heat removal may be indirect such as using a counter flow heat exchanger with boiler or it may be direct heat removal from the combustor or combustor exhaust before delivery to the expander; either way it may be said to be thermally coupled. An example of direct removal is now presented.

Figure 3A:
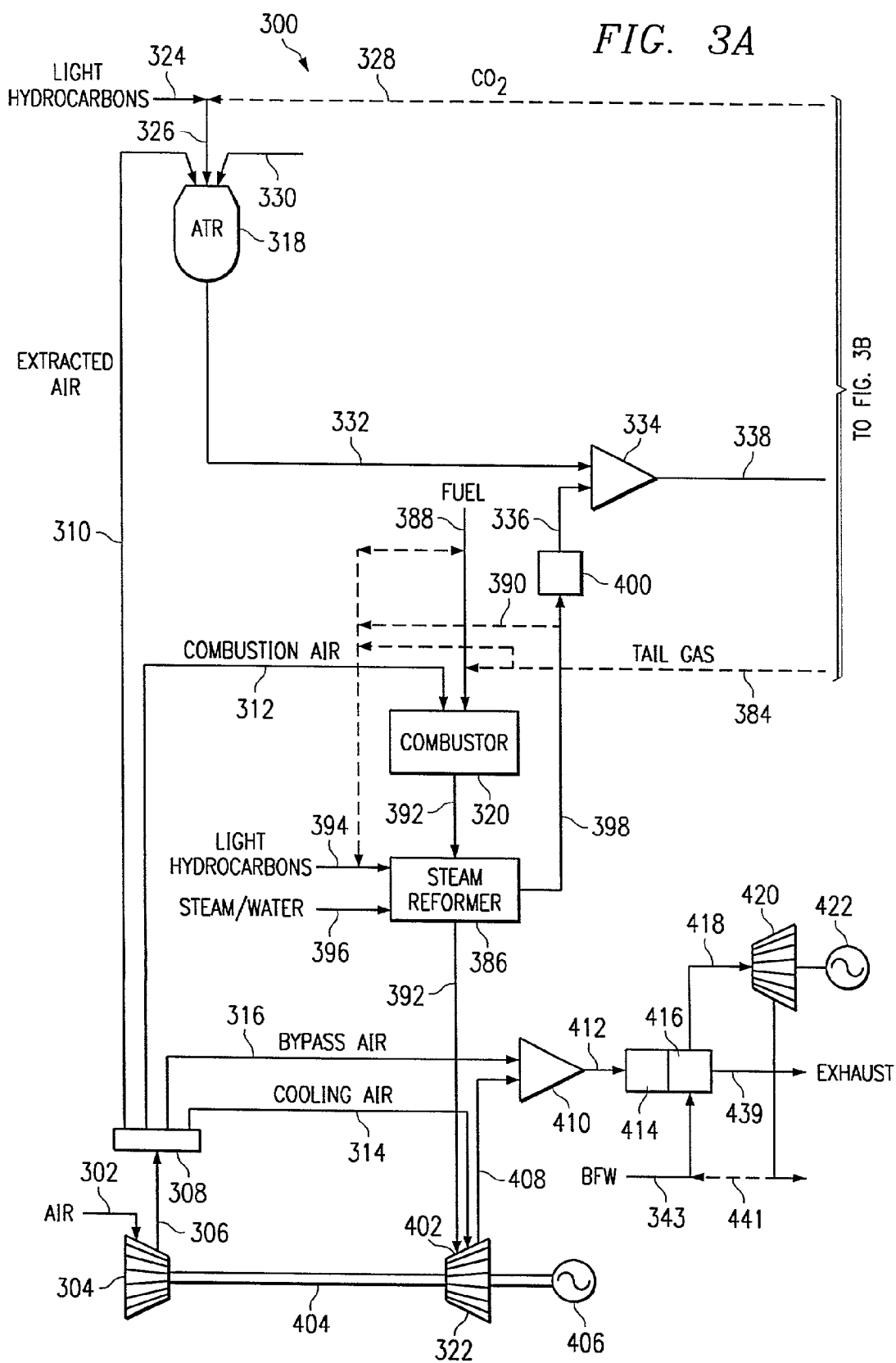
FIG. 3 is schematic diagram of another embodiment of the present invention.
Figure 3B:
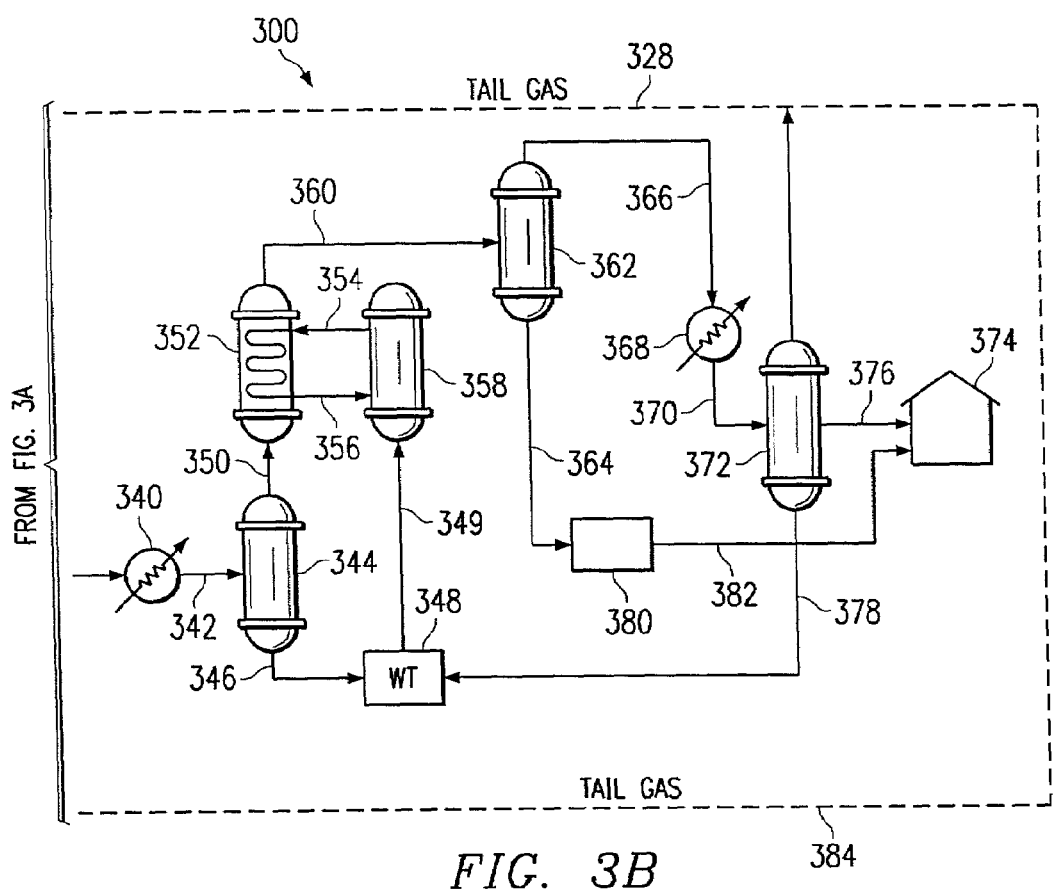

Referring now to FIG. 3 (FIGS. 3A and 3B), a system 300 for converting light hydrocarbons to heavier hydrocarbons is presented. Filtered air is delivered through conduit 302 to compressor section 304 of a gas turbine. Compressor 304 compresses the air and delivers it to conduit 306. Conduit 306 delivers the compressed air to distributor manifold 308. Distributor 308 may deliver the compressed air to four locations through conduits 310, 312, 314, 316. Conduit 310 delivers compressed air to a first synthesis gas generator 318, which is preferably an autothermal reformer (ATR). Conduit 310 (or 306) may have a membrane or other separation technology on it to produce an oxygen enriched stream. Conduit 312 delivers compressed air to combustor 320. Conduit 314 delivers air to turbine/expander 322 to assist with cooling of components such as turbine blades. Compressor 304, combustor 320, and expander 322 define a gas turbine. While combustor 320 is shown as a separate unit, it may be adjacent to or integral with expander 322.

In addition to compressed air supplied through conduit 310, light hydrocarbons (preferably natural gas) are delivered to ATR 318 through conduits 324 and 326. Those skilled in the art will appreciate that the light hydrocarbons may be pretreated prior to delivery, for example, to remove any mercaptan sulfur, to heat the gas, etc. As explained later, a $CO_2$ component of a tail gas may also be delivered to ATR 318 through conduits 328 and 326. Further still, steam/water conduit 330 may used to supply steam/water to control the molar ratio of the synthesis gas produced in the ATR 318. ATR 318 generates synthesis gas that is delivered to conduit 332.

Conduit 332 delivers synthesis gas to connector 334 where it may be combined with another source of synthesis gas (discussed later) delivered to connector 334 through conduit 336. The synthesis gas proceeds from connector 334 through conduit 338 to heat exchanger 340, which cools the synthesis gas before delivery through conduit 342 to separator 344. Condensation separated at separator 344 is delivered through conduit 346 to a water treatment subsystem 348. Subsystem 348 may be a biological treatment unit or a stripper unit to remove alcohols or other contaminants. Treated water may then be delivered through conduit 349 to steam drum 358. The gaseous effluent from separator 344 is delivered through conduit 350 to Fischer-Tropsch reactor 352. Fisher-Tropsch reactor 352 may utilize any suitable Fisher-Tropsch catalyst, such as iron, cobalt, or ruthenium and be supported such as on alumina. Reactor 352 has a closed-looped cooling unit 354 that circulates boiling feed water through conduit 356 from steam drum 358. The output of Fisher-Tropsch reactor 352 is delivered to outlet 360 from where it travels to separator 362. Separator 362 separates the Fisher-Tropsch product into a heavy F-T product that is delivered into conduit 364 and a light F-T product delivered to conduit 366. Conduit 366 delivers the light product to heat exchanger 368 (cooler) and then conduit 370 delivers the cooled product to cold separator 372.

The light F-T product enters separator 372 from conduit 370. Separator 372 distributes the liquid hydrocarbons separated therein to a storage tank or container 374 through conduit 376. Conduit 376 may include additional components such as a conventional fractionation unit. Condensation separated in separator 372 is delivered through conduit 378 to water treatment unit 348. The heavy F-T product delivered by separator 362 into conduit 364 is preferably delivered to a hydrocracker 380 or other downstream processing unit. From there, the products are delivered through conduit 382 to storage 374. Conduit 382 may include additional components such as a conventional fractionation unit. The gaseous effluent from separator 372 is a low-BTU residue gas or tail gas, which may have a heating value less than 120 BTU/SCF. The tail gas may be delivered for use as fuel as various locations in the system. The $CO_2$ component of the tail gas may be separated from the tail gas by typical separation and recovery methods known to those skilled in the art and delivered to ATR 318 and/or may be delivered through conduit 384 to a second synthesis gas generator 386, which is preferably a steam reformer. Tail gas may also be delivered to conduit 388 as a fuel for combustor 320.

Combustor 320 receives compressed air through conduit 312. It also receives fuel through conduit 388. In addition to supplied fuel to conduit 388, a synthesis gas maybe supplied to that conduit from steam reformer 386 as suggested by conduit 390. Combustor 320 exhausts its combustion products through conduit 392 which travels through steam reformer 386 where it supplies all or a substantial portion of the energy required by steam reformer 386 in producing synthesis gas. Reformer 386 may include burners to augment the heat therein. The exhaust gases preferably pass on the "shell side" of the catalyst filled reactor tubes within the steam reformer 386 as is known to those of skilled in the art. Steam reformer 386 receives light hydrocarbons, such as natural gas, through conduit 394 and steam/water through conduit 396. The steam/water and light hydrocarbons preferably pass through the "tube side" of the reformer. The tubes have an appropriate steam reforming catalyst therein, such as a promoted nickel oxide catalyst. Steam reformer 386 produces synthesis gas that is delivered to conduit 398. The synthesis gas of conduit 398 is delivered to a synthesis gas prep unit 400. Prep unit 400 may include carbon dioxide removal devices and/or a hydrogen removal device, in which case the hydrogen may be delivered to hydrocracker 380 or for use elsewhere in system 300.

After the combustor exhaust passes through steam reformer 386, it is delivered to inlet 402 of expander 322. The gases delivered to inlet 402 are expanded whereby compressor 304 is powered through linkage 404 and load 406, e.g, a generator, is powered. The turbine exhaust is delivered by conduit 408 to connector 410. From there, the exhaust gas and any bypass air from conduit 316 are delivered through conduit 412 to a heat recovery steam generator (HRSG) unit. Thereafter, the remaining exhaust exits through exhaust conduit 439. The HRSG unit may include a burner 414, a steam generator 416, and steam turbine 420. Boiling feedwater is delivered through conduit 343, and the steam is delivered through conduit 418 to steam turbine 420. Steam turbine 420 drives load 422, e.g., a second generator. The steam exhaust exiting may be condensed and the condensate delivered by conduit 441 to BFW conduit 343.

As important aspect of this embodiment, heat is directly removed from the combustion gases exiting the combustor 320 by steam reformer 386. This allows, amongst other things, more air to be extracted through conduit 310 without causing the temperature at turbine inlet 402 to become too high (i.e., causing thermal failure), and further, the inclusion of the HRSG allows for further efficiencies. Sixty percent or more the compressed air of conduit 306 may be extracted through conduit 310.

Although the present invention and its advantages have been described in detail, it should be understood that various changes, substitutions and alterations can be made therein without departing from the spirit and scope of invention as defined by the appended claims.

What is claimed is:

1. A Fischer-Tropsch-based system for converting light hydrocarbons into heavier hydrocarbons comprising:
   a gas turbine having a compressor section, combustor, and expander section, and having a compressed air conduit fluidly coupled to the compressor section for receiving compressed air from the compressor section and delivering at least a portion of the compressed air to the combustor;
   a Fischer-Tropsch hydrocarbon conversion subsystem for converting light hydrocarbons into heavier hydrocarbons;
   a heat removal subsystem associated with the combustor for thermally coupling the hydrocarbon conversion subsystem to the combustor to deliver thermal energy from the combustor to the hydrocarbon conversion subsystem;
   a process air conduit fluidly coupled between the compressed air conduit and the Fischer-Tropsch hydrocarbon conversion subsystem, the process air conduit for delivering a portion of the compressed air developed by the compressor section to the Fischer-Tropsch hydrocarbon conversion subsystem;
   wherein the heat removal subsystem comprises a heat exchanger thermally coupled to the combustor; and further comprising a steam methane reformer thermally coupled to the heat exchanger for using at least a portion of thermal energy from the combustor to prepare a first synthesis gas; and wherein the Fischer-Tropsch hydrocarbon conversion subsystem comprises:
   a synthesis gas unit for receiving natural gas, an oxygen containing gas, and steam and producing a second synthesis gas, and wherein the synthesis gas unit comprises an autothermal reformer, and
   a Fischer-Tropsch synthesis unit fluidly coupled to the synthesis gas unit for receiving the second synthesis gas therefrom and fluidly coupled to the steam methane reformer for receiving the first synthesis gas and producing heavier hydrocarbons.

2. A Fischer-Tropsch-based system for converting light hydrocarbons into heavier hydrocarbons comprising:
   a gas turbine having a compressor section, combustor, and expander section, and having a compressed air conduit fluidly coupled to the compressor section for receiving compressed air from the compressor section and delivering at least a portion of the compressed air to the combustor;
   a Fischer-Tropsch hydrocarbon conversion subsystem for converting light hydrocarbons into heavier hydrocarbons;
   a heat removal subsystem associated with the combustor for thermally coupling the hydrocarbon conversion subsystem to the combustor to deliver thermal energy from the combustor to the hydrocarbon conversion subsystem;
   a process air conduit fluidly coupled between the compressed air conduit and the Fischer-Tropsch hydrocarbon conversion subsystem, the process air conduit for delivering a portion of the compressed air developed by the compressor section to the Fischer-Tropsch hydrocarbon conversion subsystem;
   wherein the gas turbine is operable to drive a first load, and further comprising:
   a heat recovery steam generator (HRSG) unit coupled to the expander section for receiving turbine exhaust therefrom and using the exhaust to drive at least partially a second load; and
   wherein the heat removal subsystem comprises a heat exchanger thermally coupled to the combustor for receiving thermal energy from the combustor; and
   wherein the Fischer-Tropsch hydrocarbon conversion subsystem comprises:
   a steam methane reformer thermally coupled to the heat exchanger for using at least a portion of thermal energy from the combustor to prepare a first synthesis gas,
   a synthesis gas unit for receiving natural gas, an oxygen containing gas, and steam and producing a second synthesis gas, and wherein the synthesis gas unit comprises an autothermal reformer, and
   a Fischer-Tropsch synthesis unit fluidly coupled to the synthesis gas unit for receiving the second synthesis gas therefrom and fluidly coupled to the heat removal subsystem for receiving the first synthesis gas and producing heavier hydrocarbons.

3. The Fischer-Tropsch-based system of claim 2, wherein the HRSG unit comprises a burner portion, a steam generation portion for receiving thermal energy from the burner portion, and a steam turbine fluidly coupled to the steam generation portion for receiving steam therefrom and driving the second load.

* * * * *